(12) United States Patent
Ely et al.

(10) Patent No.: US 11,761,459 B2
(45) Date of Patent: Sep. 19, 2023

(54) INERTIAL PUMP FLUID DISPENSING

(71) Applicant: HEWLETT-PACKARD DEVELOPMENT COMPANY, L.P., Spring, TX (US)

(72) Inventors: Hilary Ely, Corvallis, OR (US); Pavel Kornilovich, Corvallis, OR (US); Daniel Curthoys, Corvallis, OR (US)

(73) Assignee: Hewlett-Packard Development Company, L.P., Spring, TX (US)

(*) Notice: Subject to any disclaimer, the term of this patent is extended or adjusted under 35 U.S.C. 154(b) by 601 days.

(21) Appl. No.: 16/768,883

(22) PCT Filed: Jan. 16, 2018

(86) PCT No.: PCT/US2018/013882
§ 371 (c)(1),
(2) Date: Jun. 2, 2020

(87) PCT Pub. No.: WO2019/143321
PCT Pub. Date: Jul. 25, 2019

(65) Prior Publication Data
US 2020/0368742 A1    Nov. 26, 2020

(51) Int. Cl.
| | | |
|---|---|---|
| F04F 7/00 | (2006.01) | |
| B01L 3/00 | (2006.01) | |
| F04B 43/04 | (2006.01) | |
| F04B 23/04 | (2006.01) | |

(52) U.S. Cl.
CPC ............ *F04F 7/00* (2013.01); *B01L 3/50273* (2013.01); *F04B 23/04* (2013.01); *F04B 43/046* (2013.01); *B01L 2300/0663* (2013.01); *B01L 2400/0406* (2013.01); *B01L 2400/0487* (2013.01)

(58) Field of Classification Search
CPC ....... F04F 7/00; F04B 19/006; B01L 3/50273; B01L 2400/0406
See application file for complete search history.

(56) References Cited

U.S. PATENT DOCUMENTS

| | | | |
|---|---|---|---|
| 5,496,469 A | 3/1996 | Scraggs | |
| 5,751,300 A | 5/1998 | Cowger et al. | |
| 5,982,801 A * | 11/1999 | Deak | F04F 7/00 372/39 |
| 6,949,176 B2 | 9/2005 | Vacca et al. | |
| 6,957,882 B2 * | 10/2005 | Wouters | B41J 2/17556 347/86 |
| 7,980,828 B1 * | 7/2011 | Lantz | F04B 19/006 417/207 |
| 9,090,084 B2 * | 7/2015 | Govyadinov | B41J 2/1404 |
| 2002/0197167 A1 | 12/2002 | Kornelsen | |
| 2009/0040249 A1 | 2/2009 | Wouters et al. | |
| 2010/0302313 A1 | 12/2010 | Smith | |

(Continued)

FOREIGN PATENT DOCUMENTS

| | | |
|---|---|---|
| WO | WO-1981002061 A1 | 7/1981 |
| WO | WO-2017127120 A1 | 7/2017 |

*Primary Examiner* — Reinaldo Sanchez-Medina
(74) *Attorney, Agent, or Firm* — Foley & Lardner LLP (57) ABSTRACT

A fluidic device may include a vertical fluid dispensing volume having a side outlet, a fluid channel connected to the vertical fluid dispensing volume below the side outlet and a fluid actuator asymmetrically located between ends of the fluid channel to form an inertial pump to vertically pump fluid within the channel to the side outlet.

20 Claims, 10 Drawing Sheets (56) References Cited

U.S. PATENT DOCUMENTS

| | | | |
|---|---|---|---|
| 2012/0306975 A1 | 12/2012 | Ohnishi | |
| 2014/0377145 A1* | 12/2014 | Govyadinov | B01F 25/50 |
| | | | 422/505 |
| 2015/0093838 A1 | 4/2015 | Landers et al. | |
| 2016/0341337 A1* | 11/2016 | Govyadinov | F16K 99/0019 |
| 2017/0167045 A1 | 6/2017 | Abraham | |
| 2017/0276259 A1* | 9/2017 | Govyadinov | F16K 99/0021 |
| 2019/0128248 A1* | 5/2019 | Govyadinov | F04B 19/24 |
| 2019/0143327 A1* | 5/2019 | Kornilovich | B01D 35/26 |
| | | | 422/513 |

* cited by examiner

INERTIAL PUMP FLUID DISPENSING

CROSS-REFERENCE TO RELATED APPLICATIONS

This Utility Patent Application is a U.S. National Stage filing under 35 U.S.C. § 371 of PCT/US2018/013882, filed Jan. 16, 2018, incorporated by reference herein.

BACKGROUND

Fluidic devices may be found in many applications in the biomedical field such as cell biology and protein identification. Fluidic devices are also found in other applications outside the biomedical field such as in the synthesis of chemicals, the precision dispensing of fluids, the cooling of microfluidic chips and the like. Such fluidic devices may involve the precise control over the flow of fluid. Unfortunately, precisely controlling the flow of fluid using valves and pumps often render such devices complex and expensive.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION OF EXAMPLES

Disclosed herein are example fluid flow control units and methods that facilitate precise control over the flow of fluid. Such fluid control units and methods utilize inertial pumps and gravity to precisely control the amount of fluid flow between channels and/or chambers. The disclosed fluidic device and methods utilize at least one inertial pump to vertically pump fluid within the channel against gravity to an elevated side outlet of the vertical fluid dispensing volume, wherein once the fluid is pumped to a height at or above the side outlet, the fluid may flow through the side outlet into another fluid passage or chamber. For purposes of this disclosure, the terms "vertical" or "vertically" refer to directions which are perpendicular or angled/oblique relative to a horizontal, the horizontal being perpendicular to the direction of gravity. The fluid flow control units and method provide a compact and cost-effective mechanism for controlling fluid flow, reducing or eliminating reliance upon complicated pumps and valves. As a result, the flow control units and methods are well-suited for incorporation into microfluidic chips and microfluidic devices.

In some implementations, the fluid flow control units include microfluidic channels. Microfluidic channels may be formed by performing etching, microfabrication (e.g., photolithography), micromachining processes, or any combination thereof in a substrate of the fluidic die. Some example substrates may include silicon based substrates, glass based substrates, gallium arsenide based substrates, plastic based substrates, cellulose or paper based substrates, and/or other such suitable types of substrates for microfabricated devices and structures. Accordingly, microfluidic channels, passages, chambers, orifices, and/or other such features may be defined by surfaces fabricated in the substrate of a fluidic die. Furthermore, as used herein a microfluidic channel or passage may correspond to a channel of sufficiently small size (e.g., of nanometer sized scale, micrometer sized scale, millimeter sized scale, etc.) to facilitate conveyance of small volumes of fluid (e.g., picoliter scale, nanoliter scale, microliter scale, milliliter scale, etc.).

As used herein, an inertial pump corresponds to a fluid actuator and related components disposed in an asymmetric position in a fluid channel, where an asymmetric position of the fluid actuator corresponds to the fluid actuator being positioned less distance from a first end of the fluid channel as compared to a distance to a second end of the fluid channel. Accordingly, in some examples, a fluid actuator of an inertial pump is not positioned at a mid-point of a fluid channel. The asymmetric positioning of the fluid actuator in the fluid channel facilitates an asymmetric response in fluid proximate the fluid actuator that results in fluid displacement when the fluid actuator is actuated. Repeated actuation of the fluid actuator causes a pulse-like flow of fluid through the fluid channel.

In some examples, an inertial pump includes a thermal actuator having a heating element (e.g., a thermal resistor) that may be heated to cause a bubble to form in a fluid proximate the heating element. In such examples, a surface of a heating element (having a surface area) may be proximate to a surface of a fluid channel in which the heating element is disposed such that fluid in the fluid channel may thermally interact with the heating element. In some examples, the heating element may comprise a thermal resistor with at least one passivation layer disposed on a heating surface such that fluid to be heated may contact a topmost surface of the at least one passivation layer. Formation and subsequent collapse of such bubble may generate flow of the fluid. As will be appreciated, asymmetries of the expansion-collapse cycle for a bubble may generate such flow for fluid pumping, where such pumping may be referred to as "inertial pumping."

In other examples, the fluid actuator(s) forming an inertial pump may comprise piezo-membrane based actuators, electrostatic membrane actuators, mechanical/impact driven membrane actuators, magnetostrictive drive actuators, electrochemical actuators, external laser actuators (that form a bubble through boiling with a laser beam), other such microdevices, or any combination thereof. In some implementations, the fluid actuators may displace fluid through movement of a membrane (such as a piezo-electric membrane) that generates compressive and tensile fluid displacements to thereby cause inertial fluid flow.

As will be appreciated, the fluid actuator forming the inertial pump may be connected to a controller, and electrical actuation of the fluid actuator by the controller may thereby control pumping of fluid. Actuation of the fluid actuator may be of relatively short duration. In some examples, the fluid actuator may be pulsed at a particular frequency for a particular duration. In some examples, actuation of the fluid actuator may be 1 microsecond (μs) or less. In some examples, actuation of the fluid actuator may be within a range of approximately 0.1 microsecond (μs) to approximately 10 milliseconds (ms). In some examples described herein, actuation of the fluid actuator includes electrical actuation. In such examples, a controller may be electrically connected to a fluid actuator such that an electrical signal may be transmitted by the controller to the fluid actuator to thereby actuate the fluid actuator. Each fluid actuator of an example microfluidic device may be actuated according to actuation characteristics. Examples of actuation characteristics include, for example, frequency of actuation, duration of actuation, number of pulses per actuation, intensity or amplitude of actuation, phase offset of actuation.

Disclosed herein is an example fluid flow control unit that may include a vertical fluid dispensing volume having a side outlet, a fluid channel connected to the vertical fluid dispensing volume below the side outlet and a fluid actuator within the fluid channel forming an inertial pump to vertically pump fluid within the channel to the side outlet.

Disclosed herein is an example fluid flow control method that involves supplying fluid to a fluid channel connected to a vertical fluid dispensing volume below a side outlet of the vertical fluid dispensing volume. The fluid is inertially pumped within the fluid channel vertically upward to the outlet.

Disclosed herein is an example fluid flow control unit that may include a vertical fluid dispensing volume having a side outlet, fluid channels connected to the vertical fluid dispensing volume and inertial pumps, wherein at least one inertial pump is within each of the fluid channels to pump fluid upwardly through the vertical fluid dispensing volume to the side outlet. A controller may synchronize actuations of the inertial pumps.

Figure 1:
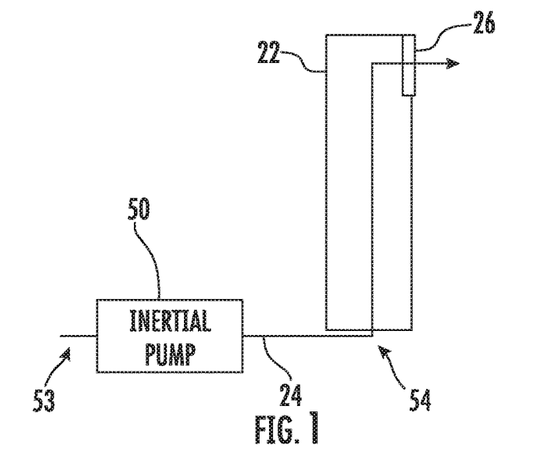
FIG. 1 is a schematic diagram illustrating portions of an example fluid flow control unit.

FIG. 1 schematically illustrates portions of an example fluid flow control unit 20 of an example fluidic device. Fluid flow control unit 20 utilizes at least one inertial pump and gravity to precisely control the amount of fluid flow between channels and/or chambers. Unit 20 provides a compact and cost-effective mechanism for controlling fluid flow, reducing or eliminating reliance upon complicated pumps and valves. As a result, unit 20 may be well-suited for incorporation into microfluidic chips and microfluidic devices. Unit 20 includes vertical fluid dispensing volume 22, fluid channel 24 and inertial pump 50.

Vertical fluid dispensing volume 22 vertically extends upwardly from fluid channel 24 and includes a side outlet 26 through which fluid is dispensed from volume. In one implementation, side outlet 26 is formed through a side wall of volume 22, adjacent an open top end of volume 22. In another implementation, side outlet 26 extends through a side wall of fluid channel 24, wherein the top of fluid channel 24 is closed or occluded. In some implementations, the top end of fluid channel 24, adjacent to an upper end of side outlet 26 may be vented. In one implementation, volume 22 includes a reservoir. In another implementation, volume 22 includes a channel or passage, wherein fluid not flowing through side outlet 26, extending through a wall of volume 22, is permitted to continue flowing past side outlet 26 in a vertically upward direction to other destinations. In one implementation, volume 22 may comprise an open topped tube, column or container, wherein side outlet 26 includes an open top of volume 22 such that fluid is permitted to flow sideways over at least one upwardly facing edge out of the container.

Fluid channel 24 includes a microfluidic channel connected to volume 22 at a height below side outlet 26. In one implementation where fluid flows through side outlet 26 under the force of gravity, side outlet 26 is at least 1 cm above a floor of channel 24. In other implementations where fluid flows through side outlet 26 by being pulled through capillary action, side outlet 26 may be closer to the floor of channel 24, such as at least 3 mm or up to at least 30 mm depending on characteristics of the fluid.

Inertial pump 50 is fluidically coupled to fluid channel 24 to vertically pump fluid within channel 24 to side outlet 26. The term "fluidically coupled" shall mean that two or more fluid transmitting volumes are connected directly to one another or are connected to one another by intermediate volumes or spaces such that fluid may flow from one volume into the other volume. In the example illustrated, inertial pump 50 includes a fluid actuator asymmetrically positioned in a fluid channel 24, where an asymmetric position of the fluid actuator corresponds to the fluid actuator being positioned less distance from a first end 53 of channel 24 as compared to a second end 54 of channel 24. The fluid actuator forming the inertial pump is not positioned at a mid-point of channel 24. The asymmetric positioning of the fluid actuator in the fluid channel 24 facilitates an asymmetric response in fluid proximate the fluid actuator that results in fluid displacement when the fluid actuator is actuated. Repeated actuation of the fluid actuator causes a pulse-like flow of fluid through fluid channel 24 and in a vertical direction, against gravity, to side outlet 26.

In some examples, an inertial pump includes a thermal actuator having a heating element (e.g., a thermal resistor) that may be heated to cause a bubble to form in a fluid proximate the heating element. In such examples, a surface of a heating element (having a surface area) may be proximate to a surface of fluid channel 24 in which the heating element is disposed such that fluid in the microfluidic channel may thermally interact with the heating element. In some examples, the heating element may comprise a thermal resistor with at least one passivation layer disposed on a heating surface such that fluid to be heated may contact a topmost surface of the at least one passivation layer. Formation and subsequent collapse of such bubble may generate inertial flow of the fluid. As will be appreciated, asymmetries of the expansion-collapse cycle for a bubble may generate such flow for fluid pumping, where such pumping may be referred to as "inertial pumping."

In other implementations, the fluid actuator forming the inertial pump 50 may comprise piezo-membrane based actuators, electrostatic membrane actuators, mechanical/impact driven membrane actuators, magnetostrictive drive actuators, electrochemical actuators, laser heating, other such microdevices, or any combination thereof. In some implementations, the fluid actuator forming the inertial pump 50 may displace fluid through movement of a membrane (such as a piezo-electric membrane) that generates compressive and tensile fluid displacements to thereby cause fluid flow.

Figure 2:
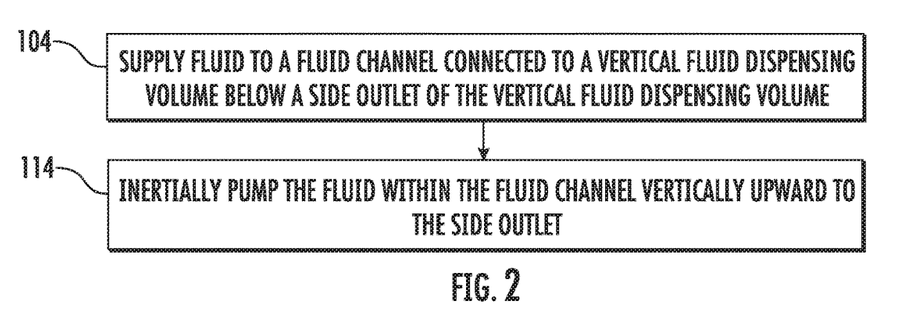
FIG. 2 is a flow diagram of an example fluid flow control method.

FIG. 2 is a flow diagram of an example method 100 for controlling the flow of fluid in a fluidic device. Method 100 utilizes at least one inertial pump and gravity to precisely control the amount of fluid flow between channels and/or chambers. Although method 100 is described in the context of being utilized or carried out by fluid flow control unit 20, it should be appreciated that method 100 may be carried out with any of the units described hereafter or with similar fluid flow control units.

As indicated by block 104, fluid is supplied to the fluid channel 24 connected to a vertical fluid dispensing volume 22 below a side outlet 26 of the vertical fluid dispensing volume 22. As indicated by block 114, the fluid within the fluid channel is inertially pumped vertically upward to the elevated side outlet 26. Through control of the inertial pump, the flow of fluid through the side outlet 26 and to the successive channel or chamber may be precisely controlled. Such control is facilitated without complex pumps or valves.

Figure 3:
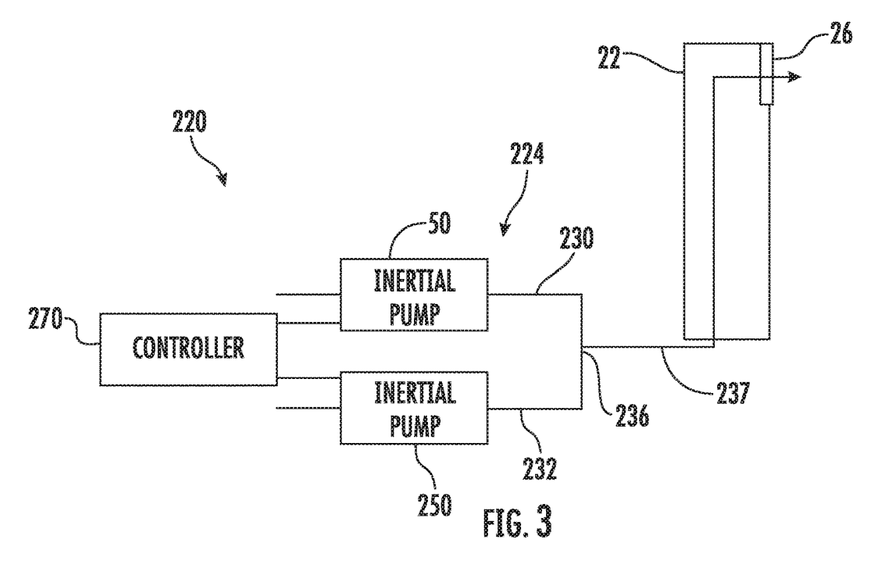
FIG. 3 is a schematic diagram illustrating portions of an example fluid flow control unit.

FIG. 3 schematically illustrates portions of an example fluid flow control unit 220. Unit 220 is similar to unit 20 described above except that unit 220 additionally includes fluid channel 224, inertial pump 250 and controller 270. Those components of unit 220 which correspond to components of unit 20 are numbered similarly.

Fluid channel 224 is similar to fluid channel 24 except that fluid channel 224 includes multiple branches 230, 232 which connect to a shared common segment 237 at a junction 236. Branches 230, 232 are connected to vertical fluid dispensing volume 22 in parallel (versus in series) with fluid channel 24. Although branches 230, 232 illustrated as being parallel to one another, branches 230, 232 may extend nonparallel to one another while still being connected in parallel to vertical fluid dispensing volume 22. Although branches 230, 232 are illustrated as being similar, in other implementations, branches 230, 232 may have different widths, shapes and/or lengths.

Inertial pumps 50 and 250 each comprise a fluid actuator or fluid displacement mechanism that is asymmetrically positioned within their respective branches 230, 232 such that actuation of pump 50 and pump 250 displaces fluid to pump fluid in a direction towards side outlet 26 of vertical fluid dispensing volume 22. Although inertial pumps 50 and 250 are illustrated as having similar asymmetries in the respective branches 230, 232, in other implementations, inertial pumps 50, 250 may have differing asymmetries in their respective branches 230, 232.

In one implementation, inertial pumps 50, 250 are the same type of inertial pumps. In other implementations, inertial pumps 50, 250 may be of different types of inertial pumps. In one implementation, both of inertial pump 50, 250 comprise thermal resistors that, in response to the application of electrical current, output sufficient heat so as to nucleate adjacent fluid and create a bubble, wherein asymmetries of the expansion-collapse cycle for a bubble may inertially pump fluid towards side outlet 26. In some implementations, inertial pumps 50, 250 may both comprise thermal resistors, but where the thermal resistors of the different inertial pumps 50, 250 have different resistor sizes, shapes or locations. Although unit 220 is illustrated as comprising two inertial pumps 50, 250 fluidicly coupled to vertical fluid dispensing volume 22 having side outlet 26, in other implementations, unit 220 may comprise additional inertial pumps also connected in parallel with pumps 50, 250 to the vertical fluid dispensing volume 22 having side outlet 26.

Controller 270 includes electronic hardware that controls the activation of inertial pumps 50 and 250. Controller 270 controls the activation of inertial pumps 50 and 250 such that pumps 50 and 250 cooperate with one another to displace fluid along branches 230, 232 and through the vertical fluid dispensing volume 22 to a sufficient elevated height such that the fluid may flow through the elevated side outlet 26. In one implementation, controller 270 includes electronic hardware in the form of an integrated circuit, such as an application-specific integrated circuit. In another implementation, controller 270 may comprise electronic hardware in the form of a processing unit that follows instructions or code contained in a non-transitory computer-readable medium.

In one implementation, shared channel segment 237 has a cross-sectional area similar to each of branches 230, 232. In such an implementation, controller 270 controls the operation of inertial pump 50 and 250 such that wave fronts of the respective fluid flow pulses are synchronized at a convergence 236 of branches 230, 232. In another implementation, junction 236 and shared channel segment 237 have a much larger cross-sectional area as compared to branches 230, 232. In such implementations, the mixing ratios of fluids from branches 230, 232, which may be delivering different fluids or types of fluids, may depend upon an average of the frequencies at which pumps 50, 250 are activated.

In one implementation, controller 270 may differently activate different inertial pumps to control a rate and/or force at which fluid is inertially pumped vertically upward in vertical fluid dispensing volume 22 through side outlet 26. For example, controller 270 may activate inertial pump 50 at a first frequency while activating inertial pump 250 at a second different frequency to control the rate of pumping or to control the time at which the level of fluid within vertical fluid dispensing volume 22 reaches side outlet 26. In implementations where system 220 includes greater than two inertial pumps connected in parallel to vertical fluid dispensing volume 22, controller 270 may actuate the different inertial pumps at different frequencies or with other differing operating parameters to control the rate at which fluid is pumped through side outlet 26 as well as the timing at which fluid is pumped through side outlet 26.

Figure 4A:
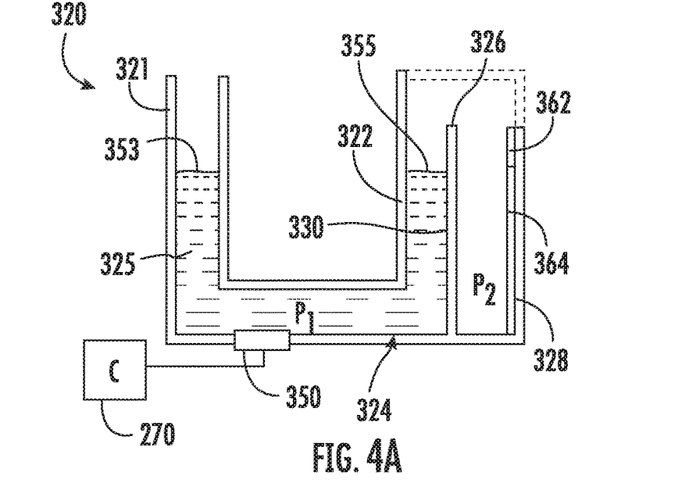
FIGS. 4A, 4B and 4C are sectional views illustrating portions of an example fluid flow control unit in different example stages of fluid delivery.
Figure 4B:
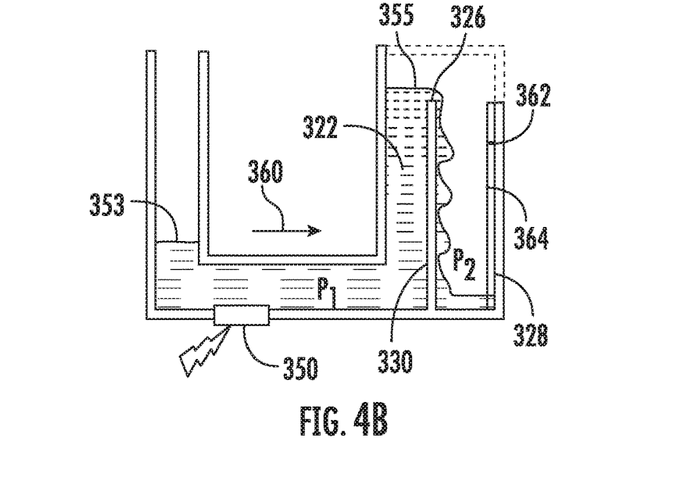
Figure 4C:
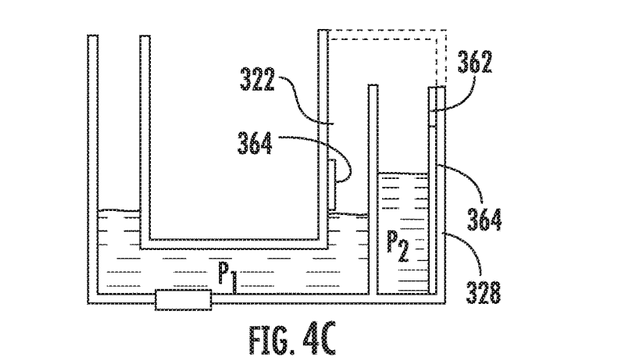

FIGS. 4A-4C illustrate the control of fluid flow by an example fluid flow control unit 320. FIG. 4A illustrates unit 320 containing fluid 325. Unit 320 includes a vertical fluid receiving volume 321, a vertical fluid dispensing volume 322 and an intermediate fluid channel 324. Volume 321, 322 and channel 324 are illustrated as containing a fluid 325 to be pumped from fluid channel 324 vertically upward through vertical fluid dispensing volume 322 through a side outlet 326 into a vertical fluid receiving channel 328. In the example illustrated, fluid channel 324 and fluid receiving volume 328 comprise distinct fluid processing regions P1 and P2. In each of such processing regions, the fluid 325 may be differently processed. For example, in a first processing region, the fluid may be mixed, heated, cooled, and/or supplemented with additional fluids or reagents. The fluid could undergo a total or partial reaction in this region. The region could also include sensors to sense the fluid properties. In the second processing region, the fluid may be further mixed, heated/cooled, sensed, supplemented with additional different fluids or reagents, undergo a reaction(s), and/or dispensed or directed to further downstream locations.

As shown by FIG. 4A, vertical fluid dispensing volume 322 and fluid receiving volume 328 are separated by an intervening wall or partition 330. Fluid vertical fluid dispensing volume 322 has an elevated side outlet 326 through which fluid may flow over our through partition 330 from volume 322 into fluid receiving volume 328. In the example illustrated, side outlet 326 is located at an upper end of partition 330. In one implementation, side outlet 326 is located at least 1 cm above the horizontal portion of fluid channel 324. As indicated by broken lines, the junction between fluid dispensing volume 322 and fluid receiving volume 328 above side outlet 326 may be closed, open or vented. In some implementations, side outlet 326 may extend through partition 330, surrounded by partition 330. The fluid to be delivered is contained within fluid receiving volume 321, fluid receiving volume 322 and channel 324, and is equilibrated by gravity within the volumes 321, 322 across channel 324.

As with fluid flow control unit 20, fluid flow control unit 320 includes an inertial pump 350 within fluid channel 324. Inertial pump 350 is asymmetrically located within a horizontal portion of fluid channel 324, interconnecting vertical volumes 321 and 322, such that activation of inertial pump 350 pumps fluid in a direction towards side outlet 326. Inertial pump 350 is located within channel 324 asymmetrically located with respect to the ends of channel 324, asymmetrically located between volume 321 and 322, so upon activation, fluid is initially pumped towards volume 322.

In one implementation, inertial pump 350 includes a thermal resistor asymmetrically located within fluid channel 324. Although illustrated as extending along the bottom of fluid channel 324, in other implementations, the thermal resistor may be located on side surfaces or top surfaces of fluid channel 324 at the asymmetric location shown. In yet other implementations, inertial pump 350 may comprise other fluid actuators such as piezo-membrane based actuators, electrostatic membrane actuators, mechanical/impact driven membrane actuators, magnetostrictive drive actuators, electrochemical actuators, external laser heater, other such microdevices, or any combination thereof. In some implementations, the fluid actuator forming the inertial pump 350 may displace fluid through movement of a membrane (such as a piezo-electric membrane) that generates compressive and tensile fluid displacements to thereby cause fluid flow.

Although FIG. 4A illustrates a single fluid channel 324 connected to vertical fluid dispensing volume 322 and containing a single inertial pump 350, it should be appreciated that vertical fluid dispensing volume 322 may likewise be connected to additional fluid channels 324 connected in parallel to the volume 322 and containing a respective inertial pump 350. As with unit 220 described above, unit 320 may comprise a controller 270 which controls the activation of the different inertial pumps 350 in the different branches that are connected in parallel to the vertical portion 334. Although volume 321 and 322 are illustrated as extending perpendicular to fluid channel 324, in other implementations, volumes 321 and 322 may vertically extend at oblique angles relative to fluid channel 324. In some implementations, vertical fluid receiving volume 321 may be omitted.

FIG. 4B illustrates activation of each of the inertial pumps 350 that are provided so as to inertially pump fluid in the direction indicated by arrow 360 until the end 355 of the column of fluid 325 rises within vertical fluid dispensing volume 322 to a height sufficient so as to flow through side outlet 326. In the example illustrated, fluid 325 spills over partition 330 into fluid receiving volume 328. By precisely controlling the activation of the inertial pump 350 or multiple inertial pumps 350, controller 270 may control the rate at which fluid 325 is provided to fluid receiving volume 328 as well as the amount or volume of fluid 325 that flows into fluid receiving volume 328. For example, controller 270 may control the frequency or rate at which the inertial pump 350 or inertial pumps 350 are activated.

FIG. 4C illustrates fluid flow control unit 320 after a selected amount of fluid 325 has been delivered to fluid receiving volume 328. In one implementation, controller 270 (shown in FIG. 4A) may activate the inertial pump(s) 350 for a predefined amount of time or at a predefined frequency so as to deliver the selected volume of fluid to fluid receiving volume 328. For example, in response to receiving a command that the selected amount of fluid 325 is to be delivered to fluid receiving volume 328, controller 270 may consult a digital lookup table indicating various parameters for the activation of the inertial pump 350 (or multiple inertial pumps 350) to deliver the selected volume.

In another implementation, controller 270 may control the activation of the inertial pump 350 to deliver the selected volume to fluid channel 328 based upon signals received from at least one fluid sensor. For example, in one implementation, unit 320 may additionally comprise at least one fluid flow sensor or flowmeter 362 within fluid receiving volume 321, fluid channel 324, fluid dispensing volume 322 and/or fluid receiving volume 328, wherein the sensed flow of fluid used to determine the amount of fluid delivered to fluid receiving volume 328. In another implementation, unit 320 may comprise at least one fluid level or presence sensor 364 that output signals indicating the current level at which fluid is present within fluid receiving volume 321, fluid receiving volume 322 and/or fluid receiving volume 328. Changes in the level of fluid within fluid volume 321, 322 or 328 may indicate the amount of fluid delivered to fluid receiving volume 328. Alternatively, the level or amount of fluid within fluid receiving volume 328 may be directly sensed with a fluid level or presence sensor 364 within fluid receiving volume 328.

Figure 5:
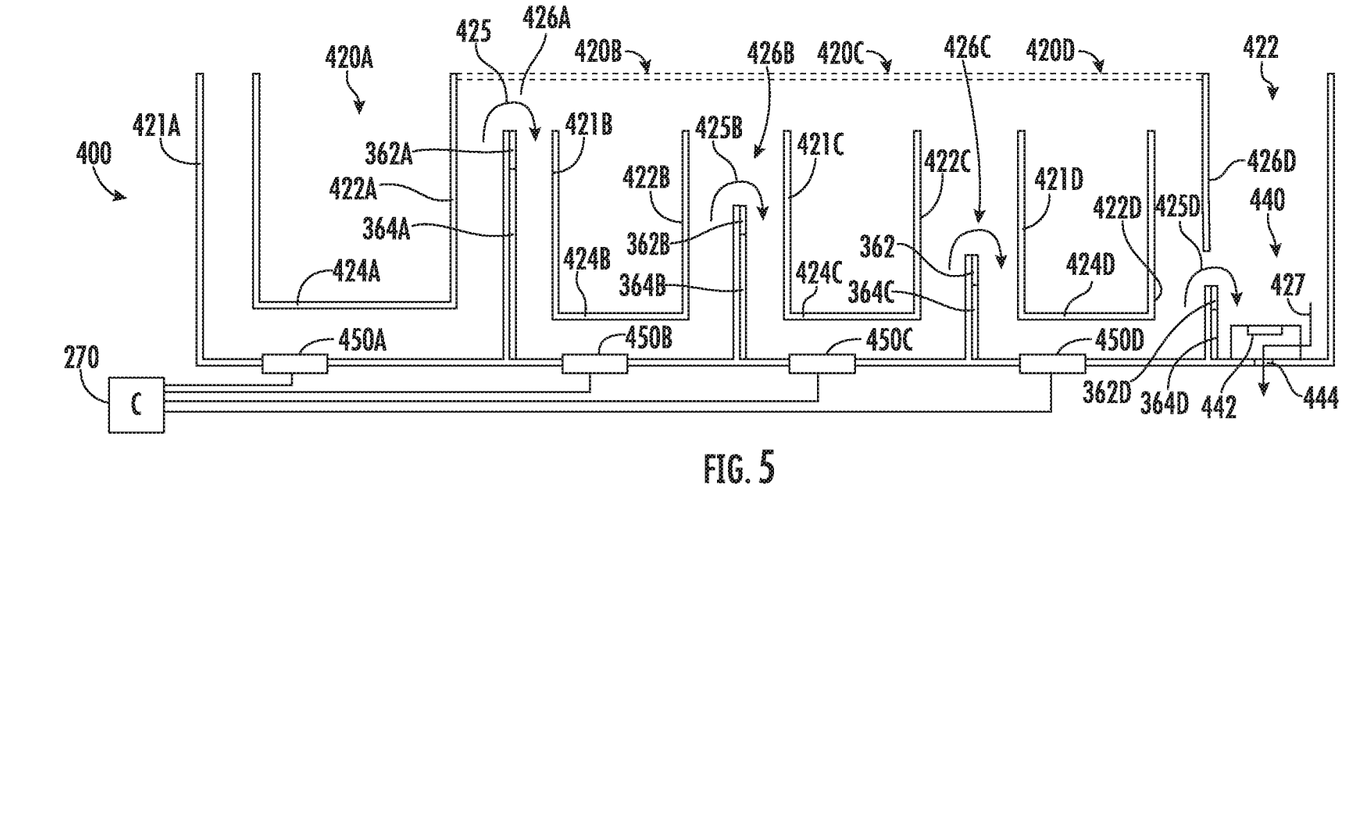
FIG. 5 is a sectional view illustrating portions of an example fluid flow control apparatus having fluid flow control units connected in series.

FIG. 5 is a sectional view illustrating portions of an example fluid flow control apparatus 400. Fluid flow control apparatus 400 includes multiple flow control units 420A, 420B, 420C, 420D (collectively referred to as flow control units 420) connected in series and under the control of a single controller 270. Flow control unit 420A delivers fluid to flow control unit 420B. Flow control unit 420B delivers fluid to flow control unit 420C. Flow control unit 420C delivers fluid to flow control unit 420D. Flow control unit 420D delivers fluid to processing channel 422. Flow control units 420A, 420B, 420C and 420D comprise fluid receiving volumes 421A, 421B, 421C, 421D (collectively referred to as fluid receiving volumes 421); fluid channels 424A, 424B, 424C and 424D (collectively referred to as fluid channels 424); vertical fluid dispensing volumes 422A, 422B, 422C and 422D (collectively referred to as volumes 422) having side outlets 426A, 426B, 426C, 426D (collectively referred to as side outlets 426); and inertial pumps 450A, 450B, 450C and 450D (collectively referred to as inertial pumps 450), respectively. In one implementation, each of flow control units 420 is similar to the other except that each successive flow control unit 420 has a side outlet vertically lower than the previous side outlet. In other implementations, the side openings or side outlets may be at a same height or other height arrangements. Side outlet 426D is lower than side outlet 426C. Side outlet 426C is lower than side outlet 426B. Side outlet 426B is lower than side outlet 426A. In one implementation each of side outlets 426 is at least 1 cm above the horizontal portion of the respective fluid channel 424. Activation of the individual inertial pumps 450 sequentially moves fluid from fluid channel 424A to fluid channel 424B (as shown by arrow 425A) to fluid channel 424C (as shown by arrow 425B), to fluid channel 424D (as shown by arrow 425C) and into processing channel 422 (as shown by arrow 425D). As shown by arrow 427, fluid may be separately dispensed from processing channel 422.

Flow control units 420 may further comprise at least one flowmeter 362 and/or at least one flow presence sensor 364, wherein signals from such sensors are utilized by controller 270 to control the staging and movement of fluid along the different flow control units 420 through the controlled activation of inertial pumps 450. In the example illustrated, flow control units 420A, 420B, 420C and 420C comprise flowmeters 362A, 362B, 362C, 362D and fluid level or presence sensors 364A, 364B, 364C and 364D, respectively. In other implementations, the flowmeters 362 and/or fluid presence sensors 364 may be omitted. In some implementations, the volume or amount of fluid delivered from one unit to the other may be controlled based upon the number and/or duration of activations of the individual inertial pumps 450 by controller 270.

Processing channel 422 includes a volume that receives fluid from fluid channel 424D. Processing channel 422 may carry out additional steps or processes upon the receipt fluid. In the example illustrated, processing channel 422 includes a dispenser to dispense fluid. In the example illustrated, processing channel 422 includes a fluid ejector 440 that includes a fluid actuator 442 located to eject fluid through a nozzle or orifice 444. In one implementation, the fluid actuator 442 includes a thermal resistor that when actuated, creates a bubble that expels fluid through orifice 444 to dispense the fluid. In other implementations, the fluid actuator 442 may comprise other fluid actuators such as piezo-membrane based actuators, electrostatic membrane actuators, mechanical/impact driven membrane actuators, magnetostrictive drive actuators, electrochemical actuators, external laser actuators, other such microdevices, or any combination thereof. In some implementations, the fluid actuator forming the fluid ejector 440 may eject fluid through movement of a membrane (such as a piezo-electric membrane) that drives fluid through orifice 444. In yet other implementations, processing channel 422 may omit fluid ejector 440. In some implementations, processing channel 422 may be connected to a reservoir or other fluid channels for carrying out other processing of the fluid.

FIGS. 6A-6D illustrate an example of processing using fluid flow control apparatus 400. For ease of illustration, fluid channels 424B-424D of fluid flow control units 420B-420D are shortened for compactness and sensors 362, 364 are omitted. It should be appreciated that the flow control units shown in FIGS. 6A-6D are as shown in FIG. 5.

Figure 6A:
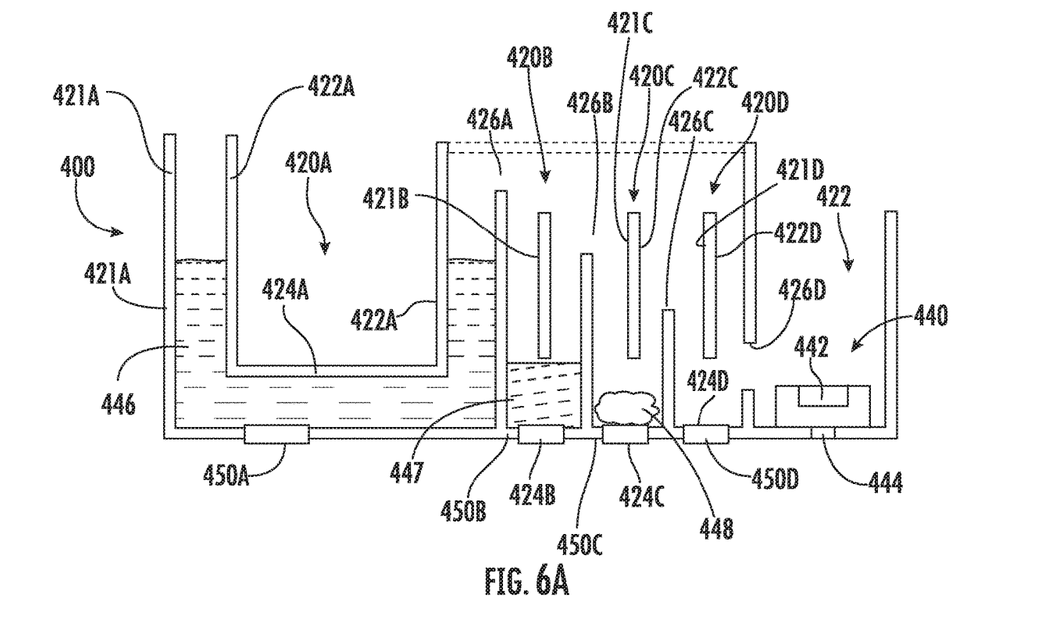
FIGS. 6A, 6B, 6C and 6D are sectional views illustrating the example fluid flow control apparatus of FIG. 5 in different example stages of fluid delivery.
Figure 6B:
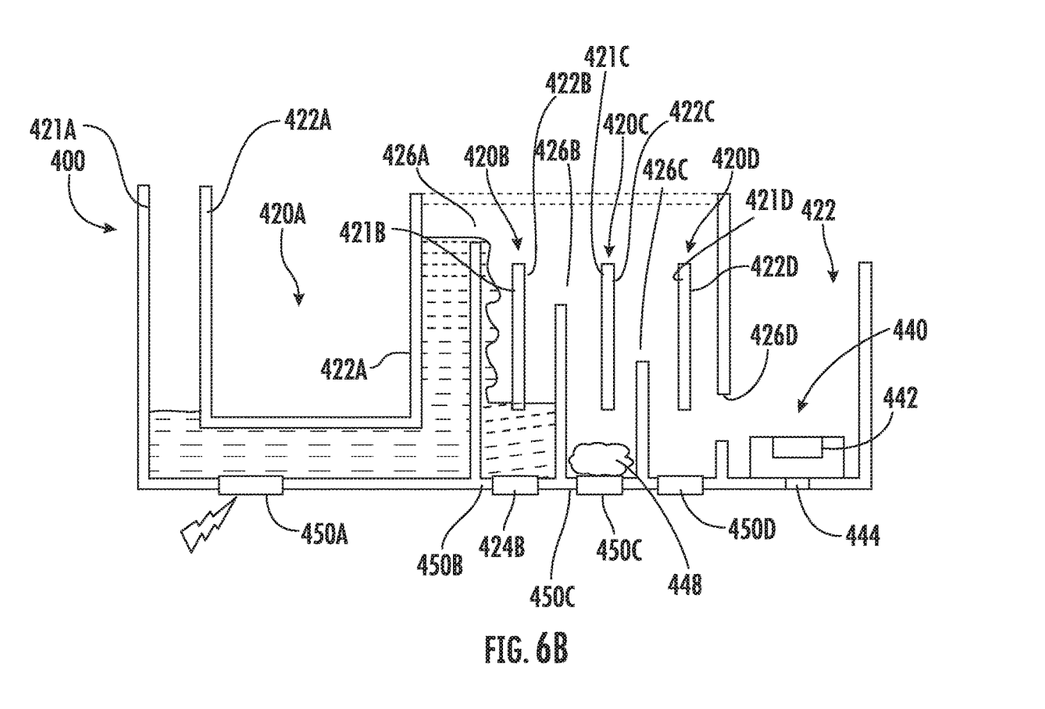

FIG. 6A illustrates flow control apparatus 400 in an initial state in which fluid channel 424A is loaded or filled with a first fluid 446, in which fluid channel 424B is filled with a second fluid 447, different than the first fluid 446, and in which fluid channel 424C contains a dried reagent 448, such as a freeze-dried reagent. FIG. 6B illustrates apparatus 400 during activation of inertial pump 450A by controller 270. As shown by FIG. 6B, pump 450A inertially pumps fluid 446 through side outlet 426A into fluid channel 424B where fluid 446 mixes with fluid 447. In one implementation, fluid 447 may comprise a reagent.

Figure 6C:
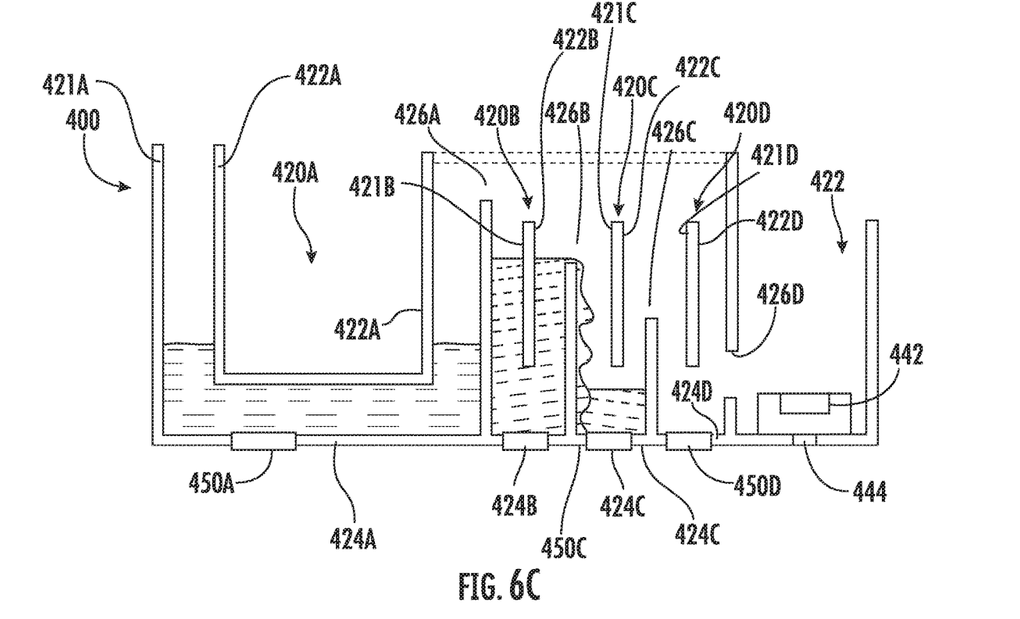

FIG. 6C illustrates flow control apparatus 400 during activation of inertial pump 450B by controller 270. As shown by FIG. 6C, pump 450B inertially pumps the mixture of fluid 446 and 447 into fluid channel 424C where fluids 446/447 come into contact with the dried reagent 448.

Figure 6D:
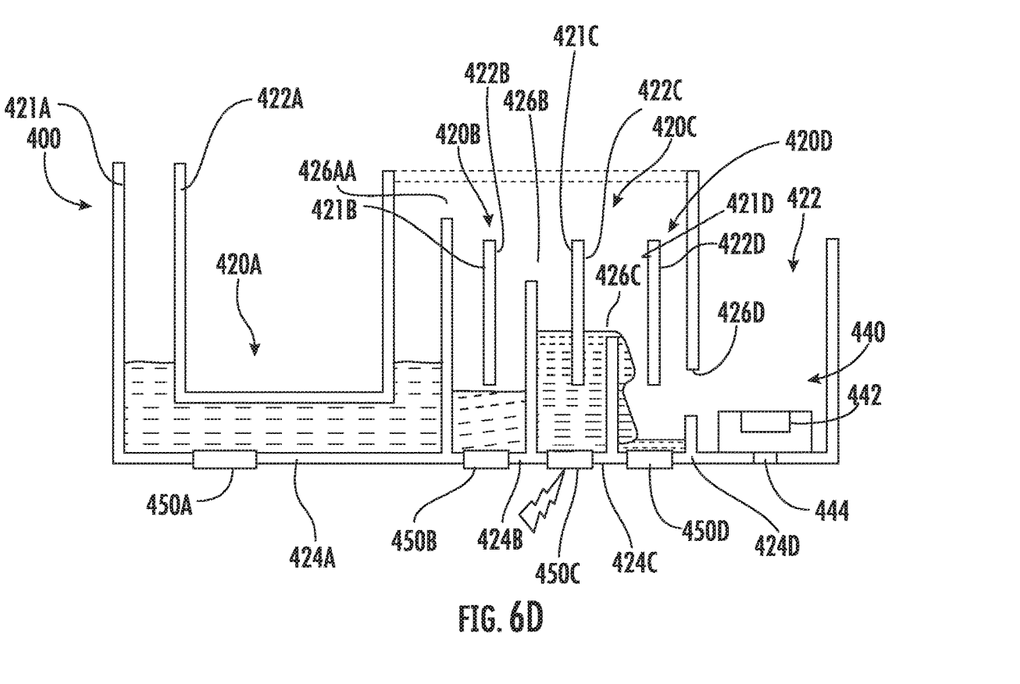

FIG. 6D illustrates flow control apparatus 400 during activation of inertial pump 450C by controller 270 which results in the fluid being further pumped downstream through side outlet 426C into fluid channel 424D. Each of fluid channels 424 may provide distinct processing of the fluid. For example, as shown in the example, different fluid channels may contain different reagents or other fluids. Different fluid channels may mix and/or heat the fluid in different manners. The control of the sequential flow of fluid between the different channels 424 facilitates sequential processing of the fluid originating in channel 424A.

Once processing has been completed in channels 424, controller 270 may activate inertial pump 450D to inertially pump the fluid through side outlet 426D into processing chamber 422. In one implementation, processing chamber 422 may carry out additional processing of the fluid, such as additional heating and/or mixing. In the example illustrated, processing chamber 422 includes fluid ejector 440 such that the fluid may be selectively and controllably ejected through orifice 444 to a destination location.

Figure 7:
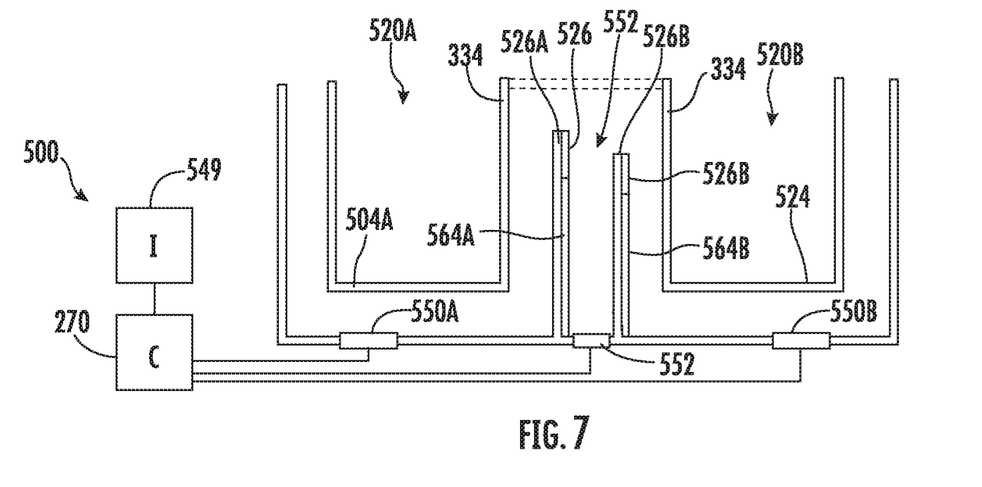
FIG. 7 is a sectional view illustrating portions of another example fluid flow control apparatus.

FIG. 7 is a sectional view illustrating portions of an example fluid control apparatus 500. Flow control apparatus 500 includes flow control units 520A and 520B (collectively referred to as flow control units 520) that controllably deliver fluid to destination fluid channel 522. Each of flow control units 520 is similar to flow control unit 220 described above. Flow control units 520A and 520B comprise vertical fluid receiving volumes 521A, 521B (collectively referred to as receiving volumes 521), vertical fluid dispensing volumes 522A, 522B (collectively referred to as volumes 522), fluid channels 524A, 524B (collectively referred to as fluid channels 524) and inertial pumps 550A, 550B (collectively referred to as an inertial pump 550), respectively. Each flow control unit 520 may comprise multiple fluid channels 524 containing an inertial pump such as described above with respect to unit 220, wherein controller 270 controls the activation of the multiple inertial pumps to inertially pump fluid upward through the vertical portion of the individual fluid channel. As further shown by FIG. 7, flow control unit 520A, 520B comprise flow meters 562A, 562B (collectively referred to as flow meters 562) and fluid level or presence sensors 564A, 564B (collectively referred to as presence sensors 564), respectively. Vertical fluid dispensing volumes 522A and 522B include vertically elevated side outlets 526A and 526B, respectively, which connect to processing channel 522.

Inertial pumps 550, flow meters 562 and fluid presence sensors 564 are similar to inertial pumps 450, flow meters 362 and fluid presence sensors 364, respectively, as described above. Inertial pumps 550 each comprise a fluid actuator, such as a thermal resistor, asymmetrically located within its respective fluid channel 524A, 524B so as to inertially pump fluid upward within a vertical portion 334 of the respective fluid channel to the side outlet 526A, 526B and into processing channel 522.

Processing channel 522 includes a processing element 552 that further interacts with the two fluids combined within processing chamber 522. In the example illustrated, processing element 552 includes a thermal resistor, under the control of controller 270, for selectively heating the mixture fluid within processing channel 522. In other implementations, processing element 522 may be omitted. Processing channel 522 may include a fluid ejector, similar to fluid ejector 440 described above, or may be connected to other channels and/or reservoirs, wherein chamber 522 guides flow of the fluid to such other chambers or reservoirs.

Figure 8:
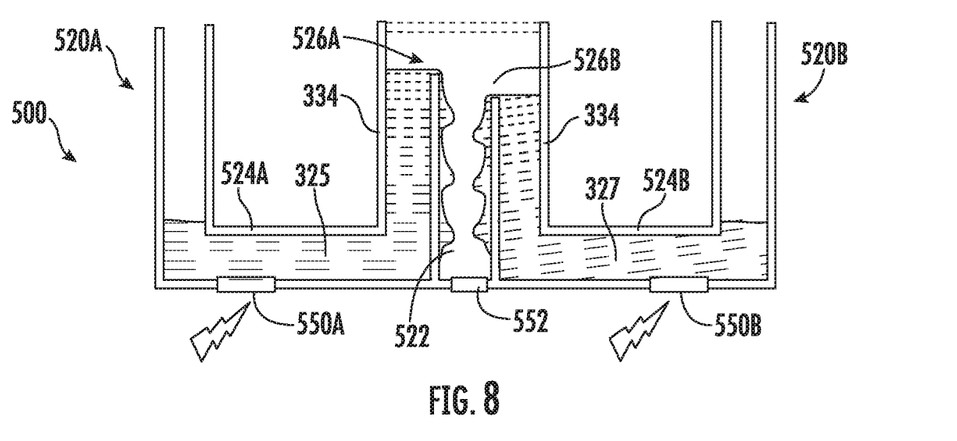
FIG. 8 is a sectional view of the example fluid flow control apparatus of FIG. 7 illustrating fluid delivery by flow control units of the fluid flow control apparatus.

FIG. 8 illustrates one example use of fluid control apparatus 500. FIG. 8 illustrates controller 270 (shown in 7) activating inertial pumps 550A and 550B to inertially pump fluid from each of fluid channels 524A and 524B into processing channel 522. In one implementation, controller 270 concurrently activates inertial pumps 550. In another implementation or when operating in a different user selected mode as received through an input, controller 270 may sequentially activate inertial pumps 550 to sequentially deliver fluid to processing channel 522. For example, in one implementation, controller 270 may output control signals initially activating inertial pump 550A so as to first pump fluid 325 into processing channel 522, allowing fluid 325 to be initially heated, mixed or react with a reagent. Thereafter, following a predetermined amount of time, the attainment of a predetermined sensed temperature or a predetermined extent of mixing, controller 270 may subsequently activate inertial pump 550B to inertially pump fluid 327 into processing chamber 522.

Figure 9:
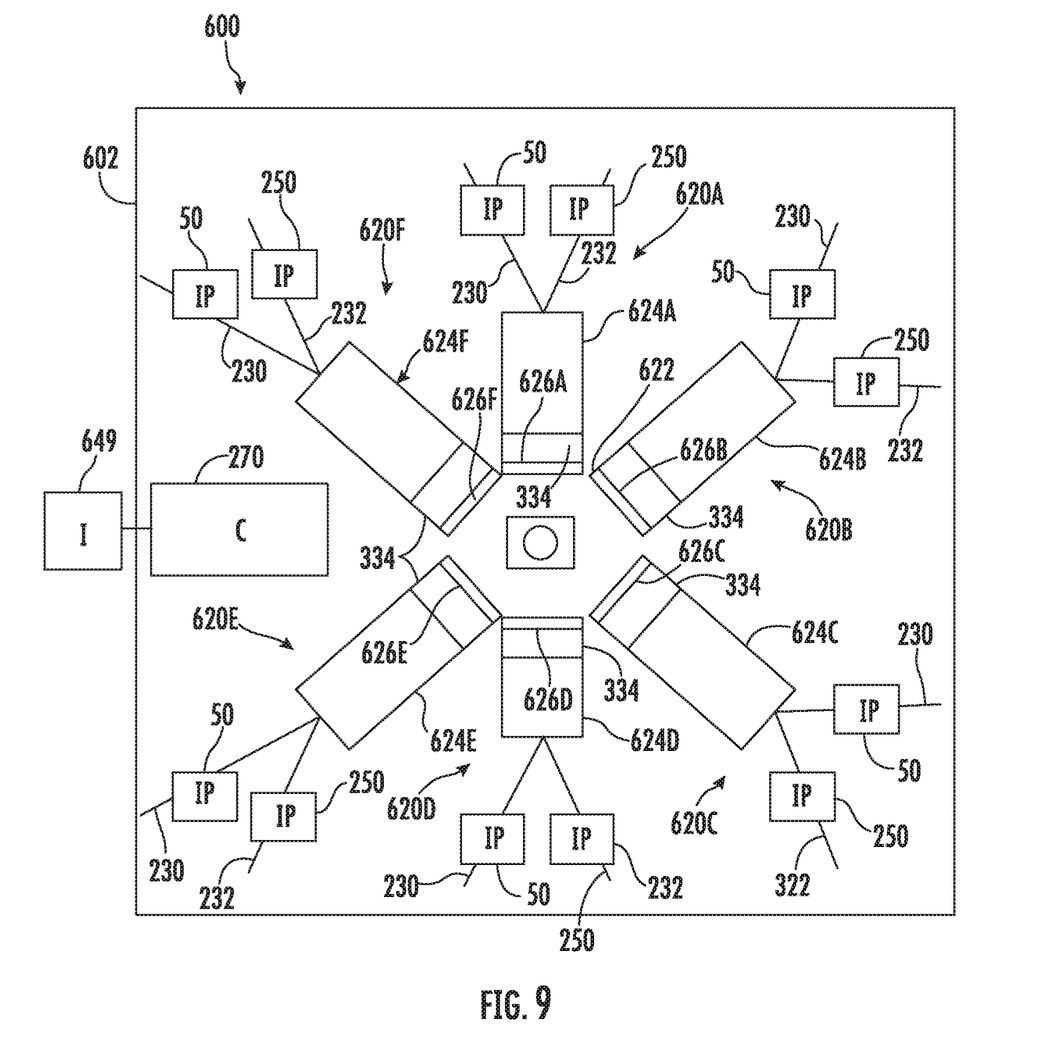
FIG. 9 is a top view of an example fluid flow control apparatus.

FIG. 9 is a top view schematically illustrating portions of an example fluid control apparatus 600. Fluid control apparatus 600 is similar to flow control apparatus 500 in that multiple flow control units may selectively deliver fluids to a single processing channel. In the example illustrated, fluid control apparatus 600 includes a chip or substrate 602 supporting flow control units 620A, 620B, 620C, 620D, 620E and 620F (collectively referred to as flow control unit 620). Each flow control unit 620 includes a vertical fluid dispensing volume 622 that is connected to a central processing channel 622 by an elevated side outlet. Flow control units 620A, 620B, 620C, 620D, 620E, 620F comprise vertical fluid dispensing volumes 622A, 622B, 622C, 622D, 622E and 622F (collectively referred to as fluid dispensing volume 622) and fluid channels 624A, 624B, 624C, 624D, 624E, 624F. Vertical fluid dispensing volumes 622A, 622B, 622C, 622D, 622E and 622F have elevated side outlets 626A, 626B, 626C, 626D, 626E, 626F, respectively. Each of fluid control unit 620 is similar to flow control unit 220. Each fluid channel 624 includes branches 230, 232, with each branch containing an inertial pump 50, 250 which are both controlled by controller 270. Each fluid channel 624 may further comprise a flow meter(s) 362 and/or fluid presence sensor 364 as shown and described above with respect to fluid channels 424. Likewise, fluid processing channel 62 may comprise a fluid level or presence sensor 364. In other implementations, fluid control apparatus 600 may include a greater or fewer of such flow control units 626 and corresponding channels 624.

Figure 10:
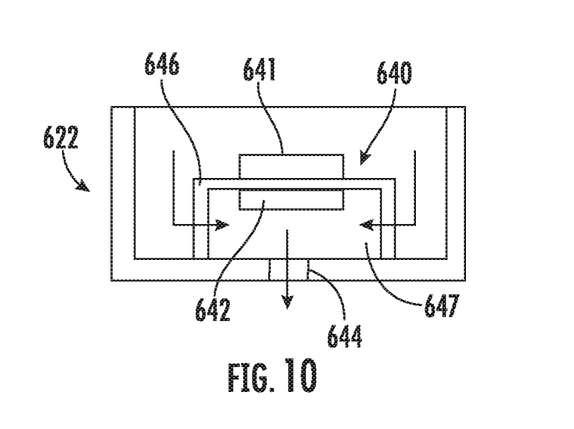
FIG. 10 is a sectional view of an example processing chamber of the example fluid flow control apparatus of FIG. 9.

FIG. 10 is a sectional view illustrating a lower portion of processing channel 622. In the example illustrated, processing channel 622 includes fluid ejector 640 and fluid heater/mixer 641. Fluid ejector 640 includes a fluid actuator 642 located to eject fluid through a nozzle or orifice 644. In one implementation, the fluid actuator 442 includes a thermal resistor that when actuated, creates a bubble that expels fluid through orifice 644 to dispense the fluid. In other implementations, the fluid actuator 642 may comprise other fluid actuators such as piezo-membrane based actuators, electrostatic membrane actuators, mechanical/impact driven membrane actuators, magnetostrictive drive actuators, electrochemical actuators, other such microdevices, or any combination thereof. In some implementations, the fluid actuator forming the fluid ejector 640 may eject fluid through movement of a membrane (such as a piezo-electric membrane) that drives fluid through orifice 644. In yet other implementations, processing channel 622 may omit fluid ejector 640. In some implementations, processing channel 622 may be connected to a reservoir or other fluid channels for carrying out other processing of the fluid.

In the example illustrated, fluid actuator 642 is supported on the underside of a platform or other structure 646 that forms an ejection chamber 647 into which fluid may flow. In the example illustrated, the top side of platform 646 supports fluid heater/mixer 641. Fluid heater/mixer 641 may comprise a fluid actuator to heat and/or mix fluid within processing channel 622 prior to the ejection of the fluid through orifice 644. In one implementation, fluid heater/mixer 641 includes a thermal resistor. The thermal resistor may heat the fluid when activated to generate a sufficient amount of heat, nucleate adjacent fluid to create a bubble that displaces fluid and mixes fluid. In other implementations, fluid actuator 642 may comprise other forms of fluid actuators. In yet other implementations, heater/mixer 641 may be omitted.

In operation, controller 270, in response to receiving commands from a user input 649, may generate control signals selectively activating the different sets of inertial pumps 50, 250 of the individual fluid control units 620 to controllably deliver different fluids from the different fluid channel 624 into processing channel 622. Controller 270 may output control signals to vary the amounts of the different fluids from the different fluid channel 624 pursuant to commands received through input 649. In one implementation, controller 270 may output control signals such that fluid is delivered to channel 622 concurrently by at least two of the fluid control unit 620. In another implementation, controller 270 may output control signals such that the selected volumes or amounts of fluid from the different control unit 620 may be delivered in a controlled order. For example, controller 270 may first activate the inertial pumps 50, 250 of unit 620A, followed by activation of the inertial pump 50, 250 of unit 620C, followed by the activation of inertial pumps 50, 250 of unit 620E and so on. In some implementations, some of the fluid channel 624 may contain different reagents while others contain analytes, wherein controller 270 may selectively activate the different control units 620 to carry out a mixing protocol.

In some implementations, controller 270 may formulate different batches of different fluids. For example, in one implementation, controller 270 may output control signals creating a first batch or mixture of fluids delivered by fluid control units 620A and 620B, wherein the mixture is ejected through orifice 644. Thereafter, controller 270 may output control signals delivering a cleaning, washing, and/or a rinsing solution to processing channel 622, wherein the solution is subsequently dispensed through orifice 644 into a receptacle. Thereafter, controller 270 may then output control signals creating a second batch or mixture of fluids delivered by fluid control unit 620D, 620E and 620F, wherein the second batch is subsequently ejected through orifice 644 at a selected destination location.

Figure 11:
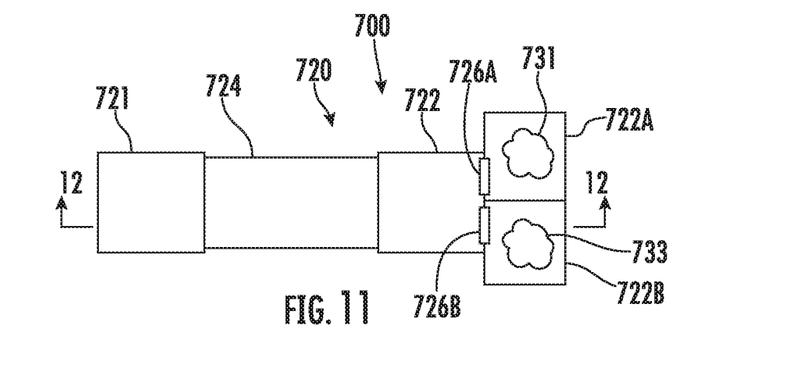
FIG. 11 is a top view of an example fluid flow control apparatus.
Figure 12:
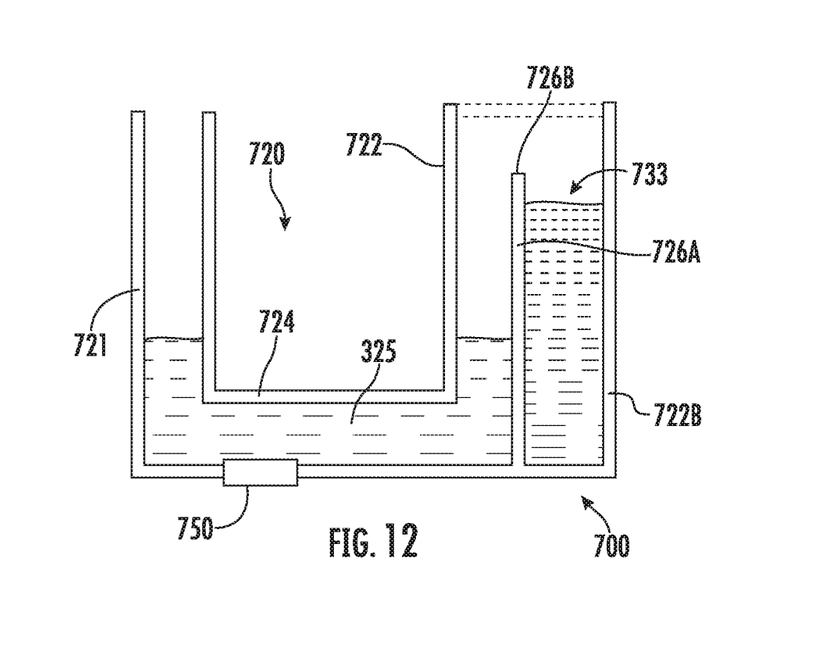
FIG. 12 is a sectional view of the fluid flow control apparatus of FIG. 11 taken along line 12-12.

FIGS. 11 and 12 schematically illustrate portions of an example fluid control apparatus 700. Fluid control apparatus 700 includes a flow control unit 720 and processing channels 722A, 722B (collectively referred to as processing channels 722). Flow control unit 720 is similar to flow control unit 624 described above. Flow control unit 720 includes a vertical fluid receiving volume 721, a vertical fluid dispensing volume 722, and a fluid channel 724 comprising a single branch or multiple branches, wherein each branch contains an inertial pump 750. Inertial pump 750 is similar to inertial pump 450 described above. Each inertial pump 750 is asymmetrically located (as described above) so as to inertially pump fluid 325 to processing channels 722.

In contrast to vertical fluid dispensing volume 622, vertical fluid dispensing volume 722 includes multiple elevated side outlets: elevated side outlet 726A connected to processing channel 722A and elevated side outlet 726B connected to processing channel 722B. In one implementation, processing channels 722A and 722B may contain different fluids and/or different reagents. In the example illustrated, processing channel 722A, prior to receipt of fluid from fluid channel 724, contains the first dried reagent 731 while processing channel 722B, prior to receipt of fluid from fluid channel 724, contains a fluid 733, such as a fluid reagent. In one implementation, processing channels 722A and 722B may comprise different elements for interacting with the received fluid, such as different heaters, mixers or fluid connections and the like. In one implementation, fluid processing channel 722A and 722B may comprise fluid ejectors, similar to fluid ejector 640 described above.

In one implementation, side outlet 726A and 726B are the same vertical height along vertical fluid dispensing volume 722 such that channels 722A and 722B concurrently receive fluid from channel 724. In another implementation, side outlet 726B is vertically above side outlet 726A (as shown in broken lines in FIG. 12) such that processing channel 722A begins receiving fluid from channel 724 prior to processing channel 722B, resulting in processing channel 722A also receiving a greater proportional amount of fluid from channel 724 as compared to processing channel 722B.

Figure 13:
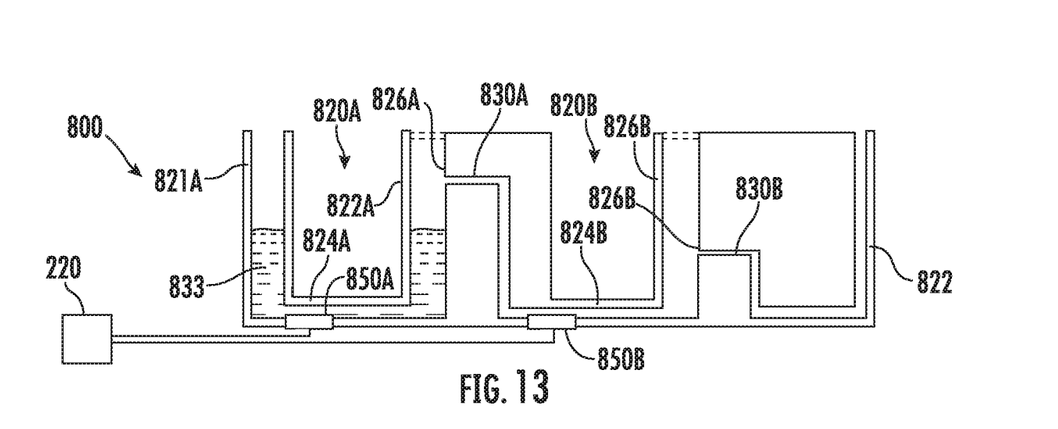
FIG. 13 is a sectional view illustrating portions of an example fluid flow control apparatus.

FIG. 13 is a sectional view illustrating portions of an example fluid control apparatus 800. Fluid control apparatus 800 is similar to fluid control apparatus 400 in that fluid control apparatus 800 includes multiple serially arranged flow control units. However, each flow control unit includes a side outlet connected to a successive flow control unit by a capillary passage, a passage that moves fluid using capillary forces. Fluid control apparatus 800 includes fluid control units 820A, 820B and processing channel 822.

Flow control unit 820A is similar to flow control unit 420. Flow control unit 820A includes vertical fluid receiving volume 821A, vertical fluid dispensing volume 822A, fluid channel 824A and inertial pump 850A. Similarly, flow control unit 820B includes vertical fluid dispensing volume 822B, fluid channel 824B and inertial pump 850B. vertical fluid dispensing volumes 822A and 822B have side outlets 826A and 826B, respectively. In the example illustrated, opening 826A is vertically higher than opening 826B. In other implementations, openings 826A and 826B may be at a same height or opening 826B may be vertically above opening 826A. Inertial pumps 850A and 850B are each similar to inertial pumps 450 described above.

As shown by FIG. 13, side outlet 826A is fluidically coupled to fluid channel 824B by a capillary passage 830A. Side outlet 826B is fluidically coupled to processing passage 822 by a capillary passage 830B. Capillary passages 830A and 830B are each dimensioned such that capillary forces pull fluid into the next channel. In the state shown in FIG. 13, fluid 833 is at equilibrium in response to gravity. When at equilibrium, fluid 833 is below side outlet 826A.

Figure 14A:
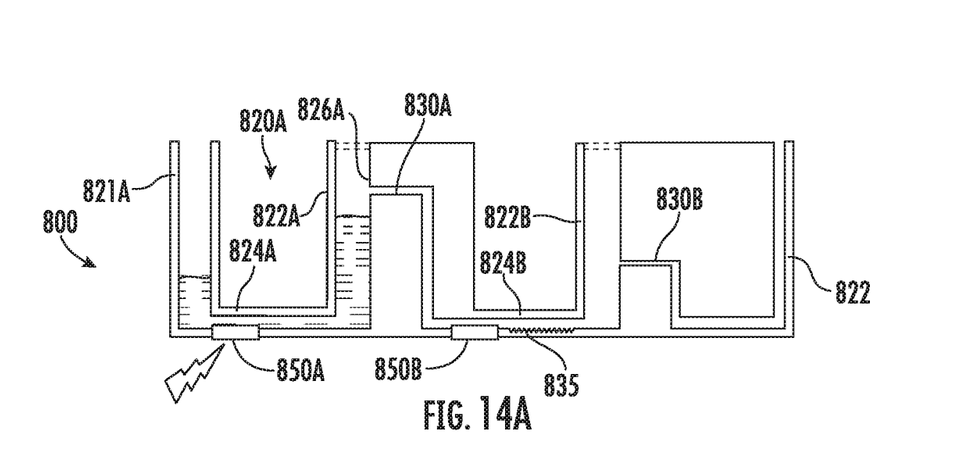
FIGS. 14A, 14B, 14D and 14D are sectional views illustrating the example fluid flow control apparatus of FIG. 13 in different stages of fluid delivery.
Figure 14B:
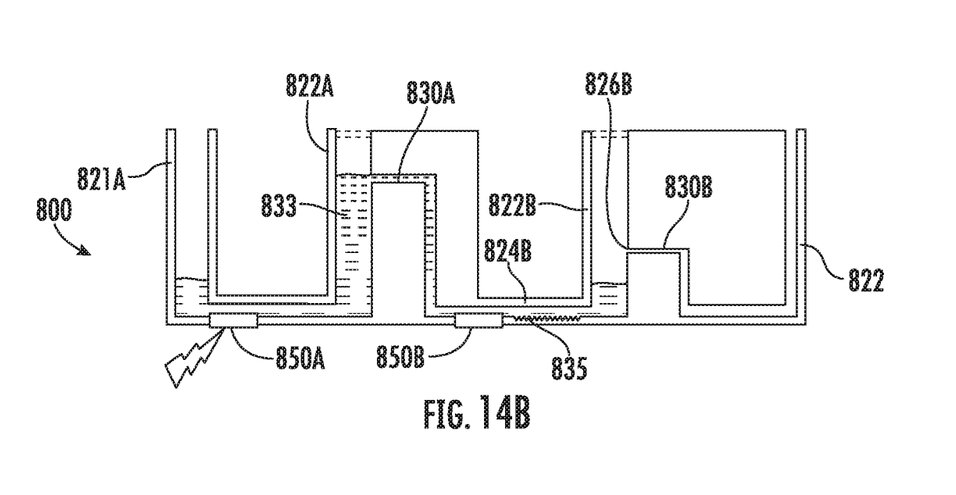
Figure 14C:
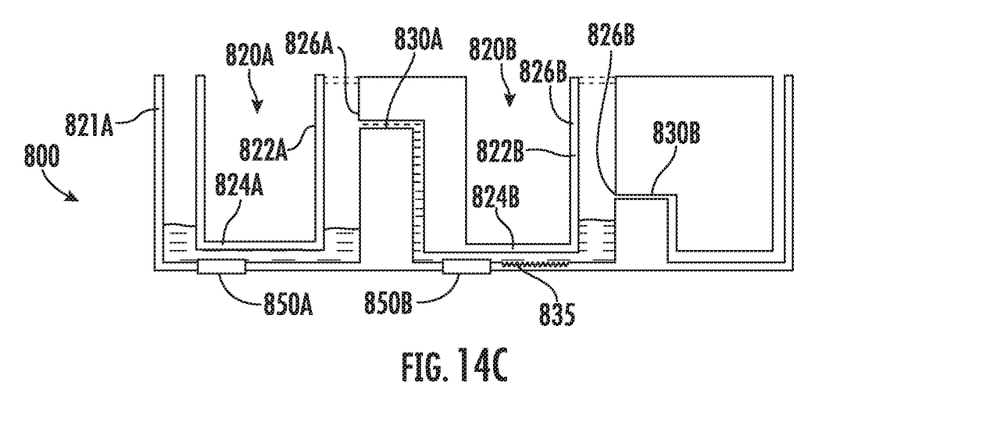

FIGS. 14A-14D illustrate fluid control apparatus 800 under the control of fluid flow by controller 270. FIG. 14A illustrates controller 270 (shown in FIG. 13) activating inertial pump 850 such that fluid 833 is inertially pumped towards side outlet 826A. FIG. 14B illustrates a continued activation of inertial pump 850A such that the level of fluid 833 within vertical dispensing volume 822A rises to a height at or above side outlet 826. As a result, fluid 833 is drawn through side outlet 826A and along capillary passage 830 into fluid channel 824B. In one implementation, fluid channel 824B may comprise a second fluid or may comprise a dried reagent, such as reagent 835. As shown by FIG. 14C, following activation of inertial pump 850A for a predetermined time or until a predetermined amount of fluid 833 has been delivered to fluid channel 824B, controller 270 ceases inertial pumping by inertial pump 850.

Figure 14D:
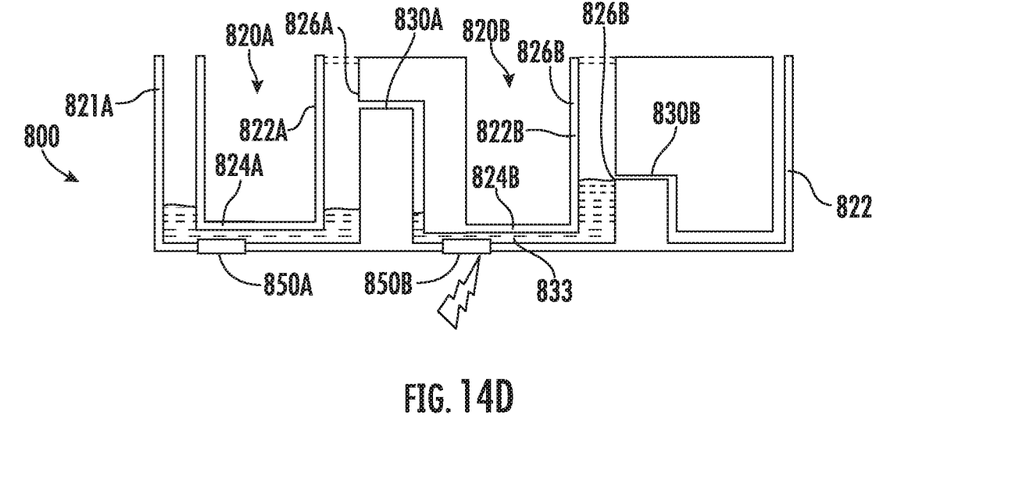

FIG. 14D illustrates controller 270 (shown in FIG. 13) activating inertial pump 850B. As a result, fluid 833, after reacting with reagent 835 and/or after being heated by a heater (which may be a thermal resistor also serving as an inertial pump 850B), is inertially pumped such as the height of the fluid 833 is at or above the elevated height of side outlet 826B. After reaching the height of side of an 826B, capillary passage 830B may pull the fluid 833 from channel 824B, through capillary forces, into processing channel 822. Processing channel 822 may be connected to other fluid channels or reservoirs. In some implementations, processing channel 822 may include additional reagents and/or additional fluids. In some implementations, processing channel 822 may comprise a fluid mixer and/or a fluid ejector such as those described above.

Although the present disclosure has been described with reference to example implementations, workers skilled in the art will recognize that changes may be made in form and detail without departing from the scope of the claimed subject matter. For example, although different example implementations may have been described as including features providing benefits, it is contemplated that the described features may be interchanged with one another or alternatively be combined with one another in the described example implementations or in other alternative implementations.

Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. A fluidic device comprising:
   a fluid channel;
   a vertical fluid dispensing volume having a top surface parallel to the fluid channel, a bottom surface parallel to the fluid channel and opposite the top surface, and a side wall orthogonal to the fluid channel, the side wall including a side outlet;
   wherein the fluid channel is connected to the vertical fluid dispensing volume below the side outlet; and
   a fluid actuator asymmetrically located between ends of the fluid channel to form an inertial pump to vertically pump fluid within the channel to the side outlet, the inertial pump comprising a heating element to heat the fluid to cause bubbles to form such that formation and subsequent collapse of the bubbles generates inertial flow of the fluid.

2. The fluidic device of claim 1 further comprising:
a second vertical fluid dispensing volume having a side wall orthogonal to the fluid channel and including a second side outlet;
a second fluid channel to receive fluid pumped from the fluid channel, the second fluid channel being connected to the second vertical fluid dispensing volume below the second side outlet; and
a second fluid actuator within the second fluid channel forming a second inertial pump to vertically pump fluid within the second fluid channel to the second side outlet.

3. The fluidic device of claim 2 further comprising:
a first fluid sensor to interact with fluid within at least one of the fluid channel and the vertical fluid dispensing volume; and
a second fluid sensor to interact with fluid within at least one of the second fluid channel and the second vertical fluid dispensing volume.

4. The fluidic device of claim 1, wherein the vertical fluid dispensing volume has a second side outlet, wherein the inertial pump vertically pumps fluid to the second side outlet, the fluidic device further comprising:
a first destination volume connected to the side outlet to receive fluid from the fluid channel; and
a second destination volume connected to the second side outlet to receive fluid from the fluid channel.

5. The fluidic device of claim 4, wherein the second side outlet is vertically above the side outlet.

6. The fluidic device of claim 1, wherein the fluid actuator comprises a thermoresistive fluid actuator.

7. The fluidic device of claim 1 further comprising:
a destination volume; and
a partition wall between the vertical fluid dispensing volume and the destination volume, wherein the side outlet comprises an opening above the partition wall such that fluid being vertically pumped by the inertial pump rises on a first side of the partition wall and falls on a second side of the partition wall into the destination volume.

8. The fluidic device of claim 1 further comprising a capillary passage extending from the side outlet.

9. The fluidic device of claim 1 further comprising:
a destination volume connected to the side outlet to receive fluid from the fluid channel;
a second vertical fluid dispensing volume having a second side outlet connected to the destination volume;
a second fluid channel connected to the second vertical fluid dispensing volume below the second side outlet; and
a second fluid actuator within the second fluid channel forming a second inertial pump to vertically pump fluid within the second fluid channel to the second side outlet.

10. The fluidic device of claim 1, wherein the fluid actuator is positioned a first distance from a first end of the fluid channel and a second distance from a second end of the fluid channel, the first distance being smaller than the second distance.

11. The fluidic device of claim 1, wherein the side outlet is formed through the side wall of vertical fluid dispensing volume adjacent an open top end of the vertical fluid dispensing volume.

12. A fluidic device comprising:
a vertical fluid dispensing volume having a side outlet;
fluid channels connected to the vertical fluid dispensing volume;
inertial pumps, wherein at least one of the inertial pumps is within each of the fluid channels to pump fluid upwardly through the vertical fluid dispensing volume to the side outlet; and
a controller to synchronize actuations of the inertial pumps.

13. The fluidic device of claim 12, the inertial pumps comprising one or more heating elements to heat the fluid to cause bubbles to form such that formation and subsequent collapse of the bubbles generates inertial flow of the fluid, the fluidic device further comprising a capillary passage extending from the side outlet.

14. The device of claim 12, wherein the controller controls the inertial pumps such that wave fronts of fluid flow pulses are synchronized at a convergence of branches of the fluid channels, the branches connecting to a shared common segment at a junction.

15. The device of claim 12, wherein the controller is configured to differently activate different inertial pumps to control a rate and/or force at which fluid is inertially pumped vertically upward in vertical fluid dispensing volume through side outlet.

16. A method for controlling fluid flow in a fluidic device, the method comprising:
supplying fluid to a fluid channel connected to a vertical fluid dispensing volume below a side outlet of the vertical fluid dispensing volume; and
inertially pumping the fluid within the fluid channel vertically upward to the side outlet wherein the inertially pumping the fluid comprises heating the fluid to cause bubbles to form such that formation and subsequent collapse of the bubbles generates inertial flow of the fluid.

17. The method of claim 16, wherein the fluid is pumped through the side outlet to a second fluid channel connected to a second vertical fluid dispensing volume below a second side outlet of the second vertical fluid dispensing volume, the method further comprising inertially pumping the fluid within the second fluid channel to the second side outlet.

18. The method of claim 17 further comprising:
interacting the fluid with a first heating element in at least one of the fluid channel and the vertical fluid dispensing volume; and
interacting the fluid with a second heating element in at least one of the second fluid channel and the second vertical fluid dispensing volume.

19. The method of claim 16, wherein the fluid is pumped through the side outlet to a destination volume, the method further comprising inertially pumping fluid within a second channel vertically upward to a second side outlet and through the second side outlet to the destination volume.

20. The method of claim 16, wherein the fluid is inertially pumped using a fluid actuator asymmetrically located between ends of the fluid channel, and wherein asymmetries of the expansion-collapse cycle for the bubbles generates inertial pumping.

* * * * *